United States Patent
Grabowski et al.

(10) Patent No.: US 6,290,990 B1
(45) Date of Patent: *Sep. 18, 2001

(54) SLOW-RELEASE MATRIX PELLETS AND THE PRODUCTION THEREOF

(75) Inventors: Sven Grabowski, Ludwigshafen; Joerg Rosenberg, Ellerstadt; Axel Sanner, Frankenthal, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/727,666

(22) PCT Filed: Apr. 15, 1995

(86) PCT No.: PCT/EP95/01236

§ 371 Date: Oct. 17, 1996

§ 102(e) Date: Oct. 17, 1996

(87) PCT Pub. No.: WO95/28147

PCT Pub. Date: Oct. 26, 1995

(30) Foreign Application Priority Data

Apr. 18, 1994 (DE) .................................................. 44 13 350

(51) Int. Cl.⁷ .............................. A61K 9/16; A61K 47/38
(52) U.S. Cl. .......................... 424/499; 424/457; 424/458; 424/468
(58) Field of Search ..................................... 424/484, 457, 424/458, 468, 499, 488; 514/952, 781

(56) References Cited

U.S. PATENT DOCUMENTS

| | | | |
|---|---|---|---|
| 3,432,592 | 3/1969 | Speiser | 424/19 |
| 4,801,460 | 1/1989 | Goertz et al. | 424/465 |
| 4,880,585 | 11/1989 | Klimesch et al. | 264/141 |
| 4,983,399 | * 1/1991 | Maish | |
| 5,552,159 | 9/1996 | Mueller et al. | 4124/464 |

FOREIGN PATENT DOCUMENTS

| | | |
|---|---|---|
| 095 123 | 11/1983 | (EP) . |
| 204 596 | 12/1986 | (EP) . |
| 388 954 | 9/1990 | (EP) . |
| 93/07859 | 4/1993 | (WO) . |

* cited by examiner

Primary Examiner—Edward J. Webman
(74) Attorney, Agent, or Firm—Keil & Weinkauf

(57) ABSTRACT

Slow-release matrix pellets with a spherical or lenticular shape and uniform maximum diameters in the range from 0.5 to 4 mm, composed of a) 0.1–87% by weight of at least one biologically active compound, b) 5–50% by weight of at least one water-insoluble polymer, c) 5–45% by weight of at least one lipophilic component as plasticizer for polymer b), d) 3–40% by weight of a natural or semisynthetic gel former, e) 0–50% by weight of one or more conventional formulation aids.

9 Claims, No Drawings

SLOW-RELEASE MATRIX PELLETS AND THE PRODUCTION THEREOF

The present invention relates to a solid, preferably pharmaceutical, slow-release form (pellets) in which the active substance is embedded in a mixture of a water-insoluble polymer, a lipid and a gel-forming polymer which in water forms a highly viscous colloidal solution or at least swells. Production takes place in a one-stage continuous process by melt extrusion and, preferably hot-cut shaping.

PRIOR ART

Matrix substances suitable for melt extrusion and slowing of release are polymers and lipids which can be plasticized by pressure and temperature. Speiser et al. describe in Pharm. Acta Helv. 46 (1971) 31 the use of epoxy/amino resins which are soluble in gastric fluid and vinyl acetate/crotonic acid copolymers which are soluble in intestinal fluid for injection-molded drug forms (cf. in this connection what is said about U.S. Pat. No. 3,432,592). Hüttenrauch and Schmeiss investigated the release of model active substances from a polyethylene matrix produced by ram extrusion (Pharmazie 30 (1975) 229, 536). Mank et al. describe in Pharmazie 44 (1989) 773 and ibid. 45 (1990) 592 the release of active substance from insoluble thermoplastic matrices. These methods do not allow the slowing of release to be adjusted freely, and the active substance is not completely released in particular from the polyethylene matrices. In addition, this process has the disadvantages of injection molding such as long residence time at high temperature and large material losses due to the feed channels whose contents must not be reused. In addition, the tooling costs are extremely high relative to the production rate.

N. A. El Gindy et al. describe in Acta Pharm. Technol. 33 (1987) 208–211 the production of tablets by melting mixtures of active substances with water-soluble (polyethylene glycols and polyoxyethylene/polyoxypropylene block copolymers) and insoluble polymers and subsequently compressing. Release from these forms is more or less rapid because of the choice of polymers. Production is by a batchwise process.

N. Follonier et al. report in Capsule News 1 (1991) 2 and in the Abstract of the 6th International Conference on Pharmaceutical Technology, Paris, France, Jun. 2–4, 1992, the production of sustained release pellets by melt extrusion from a single-screw extruder. The solidified extrudate was comminuted in a pelletizer. Water-insoluble polymers were used as matrix. Besides the size of the pellets, various additives were investigated to control release of the active substance. The polymer basis was principally an ethylene/vinyl acetate copolymer. However, it was not possible to achieve release by zero order kinetics of the active substance from these forms.

U.S. Pat. No. 3,432,592 describes the injection molding of polymer melts containing active substances. The polymers used therein are said to be at least partially soluble in the digestive fluids. The soluble polymer mainly described is a complex condensation product of an amino diol and an epoxide, which is not customary in the drugs sector. Slowing of release is achieved by also using thermoplastics of low solubility in digestive fluids. The polymer combinations indicated therein are unsuitable for slowing the release from pellets of active substances which are readily soluble in water because the surface area/volume ratio is unfavorable. In general it is difficult to control the slowing of release by this procedure, and when release is greatly slowed part of the active substance remains undissolved in the pellets (release of active substance obeys the $\sqrt{t}$ law; see T. Higuchi, J. Pharm. Sci. 52 (1963) 1145–1149). Release by zero order kinetics is not possible (cf. Table I).

EP-A 240 904 and EP-A 240 906 disclose the extrusion of polymer melts, preferably of vinylpyrrolidone copolymers, which contain active substances. There is no mention therein of the adjustment of a particular profile of active substance release by means of polymer mixtures. In addition, it has emerged that the storage stability of the products produced in this way is in many cases low, and the release-slowing effect diminishes with time.

EP-B 204 596 describes the production of pellets by embedding an active substance in a matrix composed of the following components: at least one non-hydrophilic polymer and either a mixture of at least two lipid substances, of which one has polymer-dissolving or -gelling properties and the other has lubricant properties, or one lipid substance which combines the two stated properties, with or without one or more additives selected from extenders and antistatic agents. Serious disadvantages: with higher amounts (above about 20%) of non-hydrophilic polymer the release takes place too quickly for a slow-release product, and with smaller amounts the release changes greatly on storage and is incomplete.

It is an object of the present invention to produce pellets, preferably for pharmaceutical purposes, from which the active substance is released with an adjustable release profile, ie. as slow as required, but completely. The intention was to achieve this aim by matrix pellets, ie. without release-slowing film coatings applied to the pellet core.

It is another object of the present invention, besides controlling the release of active substance by the composition of the matrix (matrix slow-release pellets), to develop a technique for simple and low-cost production of these pellets. It was intended that this take place in a continuous and one-stage process without previous mixing or pregranulation of the components and without final spheronization or similar shaping/rounding of the pellets after the production process.

ACHIEVEMENT

We have found that this object is achieved in a simple manner by melt extrusion of certain polymer matrices which contain active substances and subsequent continuous shaping to produce slow-release pellets with high active substance content, even of active substances which are very readily soluble in water, it being possible to achieve release profiles which can be adjusted over wide ranges solely by the composition of the polymer matrix without diffusion-controlling polymer coatings and which have high storage stability.

The basic principle of the polymer matrix according to the invention is a matrix which is plasticized by suitable lipophilic substances and is composed of a polymer which is insoluble in water and gastrointestinal fluids. In contrast to the prior art cited above, it is now possible to adjust the release profile freely over wide ranges if the matrix of insoluble polymer and lipophilic component additionally incorporates a gel former, ie. a polymer which in water forms a highly viscous solution (hydrocolloid) or at least swells. With the prior art matrices, although the release of the active substance is controlled by the concentration of insoluble polymer, there is a risk that the administration form will disintegrate if the amount of polymer is too low, but the release of active substance may be incomplete if the amount of polymer is too large, since portions of the active substance are completely entrapped and unavailable. The addition, according to the invention, of gel former breaks up the release-slowing matrix by swelling of this polymer, and the active substance can be completely released (cf. Tab. I).

The polymer matrix according to the invention for matrix slow-release pellets is a novel combination of inert, lipophilic and hydrophilic thermoplastic matrix.

The invention therefore relates to a solid pharmaceutical slow-release form (matrix pellets) produced in a single-stage process by melt extrusion in an extruder, preferably a twin-screw extruder or a single-screw extruder with mixing section, at 50–200° C. with continuous (preferably hot-cut) shaping of a mixture of the following composition:

a) at least one biologically active compound ("active substance"; preferably in human or veterinary medicine, but also vitamins and systemic insecticides, fungicides and herbicides) in an amount of 0.1–87, preferably 1–75, in particular 45–75, % by weight, b) at least one natural, semisynthetic or synthetic polymer which is insoluble in water and gastrointestinal fluids, in an amount of 5–50, preferably 10–40, % by weight, c) 5–45, preferably 10–35, % by weight of at least one water-insoluble lipophilic component with plasticizer properties for polymer b) and lubricant properties, d) 3–40, preferably 5–25, % by weight of at least one natural or semisynthetic hydrophilic polymer which in water or gastrointestinal fluids forms highly viscous colloidal solutions or gels or at least swells (abbreviated to "gel former" herein), and e) 0–50, preferably 0–40, % by weight of one or more conventional formulation auxiliaries.

The percentage data in each case are based on the total weight of the pellets.

Solid pharmaceutical slow-release forms for the purpose of the invention are, for example, granules, preferably pellets, with delayed release of active substance. The resulting shaped articles can also be subsequently milled to a powder and used in this form (e.g. in hard gelatin capsules). Subsequent coating of the shaped articles with flavor-masking film coatings as in the prior art (e.g. with polyacrylates, cellulose esters such as hydroxypropylmethylcellulose phthalates and cellulose ethers such as ethylcellulose, hydroxypropylmethylcellulose or hydroxypropylcellulose) is not precluded but is as a general rule unnecessary.

The pellets can in many cases be compressed to tablets. This compression is suitable, inter alia, in cases where the dose of active substance is high and thus the resulting drug forms would be undesirably large. It is possible by controlling the tabletting conditions (in particular the pressure) for individual pellets to disintegrate in some circumstances, so that the release of active substance does not have to be essentially different from analogous pellets which have been packed (loosely) in capsules. Compression to tablets leads to a reduction in volume of the drug form, which may be advantageous in some cases. It is furthermore possible, by adding osmotically active agents (e.g. inorganic salts), to obtain pellets which can be used as osmotically active swelling layer (cf. WO 92/04011) in order to bring about the release of active substance, e.g. from tablets (after compression) or capsules, by an osmosis principle.

Pharmaceutical active substances a) for the purpose of the invention mean all substances with a pharmaceutical action and minimal side effects as long as they do not decompose under the processing conditions. The amount of active substance per dose unit and the concentration can vary within wide limits depending on the activity and desired rate of release. The only condition is that they are such to achieve the desired action. Thus, the active substance concentration can be in the range from 0.1 to 87, preferably 1 to 80, in particular 45 to 75, % by weight. Active substances for the purpose of the invention are also, as mentioned, other biologically active compounds. Those preferred are betamethasone, thioctic acid, sotalol, salbutamol, norfenefrine, silymarin, dihydroergotamine, buflomedil, etofibrate, indomethacin, oxazepam, beta-acetyldigoxin, piroxicam, haloperidol, ISMN, amitriptyline, diclofenac, nifedipine, verapamil, pyritinol, nitrendipine, doxycycline, bromhexine, methylprednisolone, clonidine, fenofibrate, allopurinol, pirenzepine, levothyroxine, tamoxifen, metildigoxin, o-(beta-hydroxyethyl)rutoside, propicillin, aciclovir mononitrate, paracetamol, naftidrofuryl, pentoxyfylline, propafenone, acebutolol, L-thyroxine, tramadol, bromocriptine, loperamide, ketotifen, fenoterol, Ca dobesilate, propranolol, minocycline, nicergoline, ambroxol, metoprolol, beta-sitosterol, enalapril hydrogen maleate, bezafibrate, ISDN, gallopamil, xanthinol nicotinate, digitoxin, flunitrazepam, bencyclane, dexapanthenol, pindolol, lorazepam, diltiazem, piracetam, phenoxymethylpenicillin, furosemaide, bromazepam, flunarizine, erythromycin, metoclopramide, acemetacin, ranitidine, biperiden, metamizole, doxepin, dipotassium chlorazepate, tetrazepam, estramustine phosphate, terbutaline, captopril, maprotiline, prazosin, atenolol, glibenclamide, cefaclor, etilefrine, cimetidine, theophylline, hydromorphone, ibuprofen, primidone, clobazam, oxaceprol, medroxyprogesterone, flecainide, Mg pyridoxal 5-phosphate glutamate, hymecromone, etofylline clofibrate, vincamine, cinnarizine, diazepam, ketoprofen, flupentixol, molsidomine, glibornuride, dimetindene, melperone, soquinolol, dihydrocodeine, clomethiazole, clemastine, glisoxepide, kallidinogenase, oxyfedrine, baclofen, carboxymethylcysteine, thioridazine, betahistine, L-tryptophan, myrtol, bromelains, prenylamine, salazosulfapyridine, astemizole, sulpiride, benserazide, dibenzepin, acetylsalicylic acid, miconazole, nystatin, ketoconazole, Na picosulfate, colestyramine, gemfibrocil, rifampicin, fluorocortolone, mexiletine, amoxicillin, terfenadine, mucopolysaccharide polysulfates, triazolam, mianserin, tiaprofenic acid, amezinium metilsulfate, mefloquine, probucol, quinidine, carbamazepine, Mg L-aspartate, penbutolol, piretanide, amitriptyline, cyproterone, Na valproate, mebeverine, bisacodyl, 5-aminosalicylic acid, dihydralazine, magaldrate, phenprocoumon, amantadine, naproxen, carteolol, famotidine, methyldopa, auranofin, estriol, nadolol, levomepromazine, doxorubicin, meclofenoxate, azathioprine, flutamide, norfloxacin, fendiline, prajmalium bitartrate, escin.

Solid solutions of the following active substances are particularly preferred: acetaminophen (=paracetamol), acetohexamide, acetyldigoxin, acetylsalicylic acid, acromycin, anipamil, benzocaine, beta-carotene, chloramphenicol, chlordiazepoxide, chlormadinone acetate, chlorthiazide, cinnarizine, clonazepam, codeine, dexamethasone, diazepam, dicumarol, digitoxin, digoxin, dihydroergotamine, drotaverine, flunitrazepam, furosemide, gramicidine, griseofulvin, hexobarbital, hydrochlorothiazide, hydrocortisone, hydroflumethazide, indomethacin, ketoprofen, lonetil, medazepam, mefruside, methandrostenolone, methylprednisolone, methylsulfadiazine (=sulfaperin), nalidixic acid, nifedipine, nitrazepam, nitrofurantoin, nystatin, estradiol, papaverine, phenacetin, phenobarbital, phenylbutazone, phenytoin, prednisone, reserpine, spironolactone, streptomycin, sulfadimidine (=sulfamethazine), sulfamethizole, sulfamethoxazole, sulfameter, sulfaperin, sulfathiazole, sulfisoxazole, testosterone, tolazamide, tolbutamide, trimethoprim, tyrothricin.

The term "solid solutions" is familiar to the skilled worker, see Chiou and Riegelman, J. Pharm. Sci. 60 (1971) 1281–1302. Active substances in solid solutions in polymers are present in a molecular dispersion in the matrix.

The natural, semisynthetic or synthetic polymer b) which is insoluble in water and gastrointestinal fluids can be, for example, a cellulose ether such as ethylcellulose or a cellulose ester such as cellulose diacetate, cellulose triacetate, cellulose acetate propionate and cellulose acetate butyrate. It is also possible to use insoluble polysaccharides such as chitin and chitin derivatives and microcrystalline cellulose. Examples of suitable synthetic polymers are poly(meth)acrylates, homo- and copolymers of vinyl acetate, and the like. Ethylcelluloses are preferred.

The water-insoluble lipophilic component c) with plasticizing properties for the polymer b) and lubricant properties can be, for example, a fatty alcohol such as cetyl or stearyl alcohol, a fatty acid such as stearic acid or a wax, for example ester wax based on montan wax. It is also possible to use according to the invention, for example, polyethoxylated fatty alcohols, fatty acids and vegetable oils, hydrogenated vegetable oils, mono-, di- and triglycerides as well as lecithins. It is furthermore possible to use polyglycerol fatty acid esters, saturated polyethoxylated glycerides, polyethylene oxides, polypropylene oxides and block copolymers thereof, phthalic esters and acetylated monoglycerides. Mono-, di- or triglycerides or mixtures thereof and polyglycerol fatty acid esters are preferred. Lipophilic components c) with an HLB (hydrophilic/lipophilic balance) of 1–9, in particular 2–5, are preferred.

Suitable gel formers d), ie. polymers which in water form highly viscous colloidal solutions or gels or at least swell, are, in particular, water-soluble cellulose derivatives such as alkylcelluloses, hydroxyalkylcelluloses, hydroxyalkylalkylcelluloses, e.g. methylcellulose, hydroxymethylcellulose, hydroxyethylcellulose, hydroxypropylcellulose, hydroxybutylcellulose, hydroxyethylmethylcellulose, hydroxypropylmethylcellulose; also carboxyalkylcelluloses, carboxyalkylalkylcelluloses, carboxyalkylcellulose esters, e.g. carboxymethylcellulose and its alkali metal salts; they may also be other water-soluble polysaccharides such as alginic acids and their salts (alginates), carrageenans, guar gum, xanthan gum, agar—agar, gum arabic and related gums, pectins, galactomannans, tragacanth, also water-soluble chitin derivatives such as chitosan. Water-soluble alkylcelluloses, hydroxyalkylcelluloses or hydroxyalkylalkylcelluloses which as a 2% strength solution in water at 20° C. have a viscosity of more than 1000 cps, preferably 3500–120,000 cps, are preferred. Hydroxypropylmethylcelluloses with a degree of methylation of 1.36–1.81 and a degree of hydroxypropylation of 0.12–0.23, as well as hydroxypropylcelluloses, are very particularly preferred.

Synergistic increases in viscosity by mixing the polymeric components, for example hydroxypropylcelluloses with anionic polymers such as carboxymethylcelluloses or sodium alginate, are particularly advantageous.

"Water-soluble" means that at least 0.5, preferably at least 2, grams of the polymer form a colloidal solution in 100 grams of water at 20° C.

Also suitable as polymer component d) are hydrophilic polymers which are insoluble in water or intestinal fluids but swellable, such as crosslinked polyvinylpyrrolidone or crosslinked starches, starch derivatives such as sodium starch glycolate, croscarmellose sodium, hydroxypropylcellulose with a low degree of substitution and crosslinked sodium carboxymethylcellulose with a low degree of substitution.

It is crucial for the suitability of a polymer as component d) that, on the one hand, it is hydrophilic and, on the other hand, it does not dissolve too rapidly in the digestive tract. On the one hand, it should permit the active substance to diffuse out of the interior of the pellets but, on the other hand, this should take place only slowly. This is why it should form a gel or a highly viscous solution with water. The choice of this component and its amount has a crucial influence on the release-slowing effect. It has emerged, surprisingly, that the abovementioned natural or semisynthetic hydrophilic gel-forming polymers ensure, in contrast to completely synthetic polymers such as PVP or vinylpyrrolidone/vinyl acetate copolymers, high storage stability (release-slowing effect is constant on storage).

Component e) can be composed of one or more auxiliaries conventional for such purposes, such as fillers, lubricants, mold release agents, plasticizers, blowing agents, stabilizers, dyes, extenders, flow regulators and mixtures thereof. Examples of fillers are inorganic fillers such as the oxides of magnesium, aluminum, silicon, titanium etc. and microcrystalline cellulose and cellulose powder, various starches and their breakdown products, (maltodextrins), lactose, mannitol and calcium diphosphate in a concentration of 0.02–50, preferably 0.20–20, % of the total weight of the pellets.

Examples of lubricants are stearates of aluminum and calcium, and talc and silicones in a concentration of 0.1–5, preferably 0.1–3, % of the total weight of the pellets.

Examples of plasticizers comprise low molecular weight poly(alkylene oxides) such as poly(ethylene glycols), poly(propylene glycols), poly(ethylene/propylene glycols); organic plasticizers with a low molecular weight, such as glycerol, pentaerythritol, glycerol monoacetate, diacetate or triacetate, propylene glycol, sorbitol, sodium diethyl sulfosuccinate, added in concentrations of 0.5–15, preferably 0.5–5, % of the total weight of the pellets.

Examples of dyes are known azo dyes, organic and inorganic pigments, or coloring matter of natural origin. Inorganic pigments are preferred and are present in concentrations of 0.001–10, preferably 0.5–3, % of the total weight of the pellets.

Auxiliaries also mean for the purpose of the invention substances for producing a solid solution containing the pharmaceutical active substance. Examples of these auxiliaries are sugars and sugar alcohols such as mannitol, sorbitol, xylitol, also urea, pentaerythritol and pentaerythritol tetraacetate, polymers such as polyethylene oxides and polypropylene oxides and block copolymers thereof (poloxamers), phosphatides such as lecithin, homo- and copolymers of vinylpyrrolidone, surfactants such as polyoxyethylene 40 stearate and citric and succinic acids, bile acids, sterols and others, as indicated, for example, in J. L. Ford, Pharm. Acta Helv. 61 (1986) 69–88.

Also regarded as pharmaceutical auxiliaries are bases or acids added to control the solubility of an active substance (see, for example, K. Thoma et al., Pharm. Ind. 51 (1989) 98–101).

The active substance or substances can be mixed with the polymeric binders and, where appropriate, other conventional pharmaceutical additives before or after the melting of the polymeric binder by conventional industrial processes. The mixing preferably takes place in an extruder, preferably in a twin-screw extruder or a single-screw extruder with a mixing section.

The mixture of polymeric binders should, in the complete mixture of all the components, soften or melt in the range from 50 to 200, preferably 50 to 180, in particular 60 to 150, ° C. so that the composition can be extruded.

The melts contain no solvent. This means that no water and no organic solvent is added.

The shaping takes place by melt extrusion at 50–200, preferably 50–180, in particular 60–150, ° C. and subsequent continuous forming to tablets, for example as described in EP-A 240 906 by passing the extrudate between two rolls driven in opposite directions with mutually opposing recesses, whose design determines the shape of the tablets, in the surface of the rolls. Cold-cut shaping is also suitable.

Hot-cut shaping is preferred. This entails the extrudates being comminuted immediately after emerging from the die arrangement on the extruder by, for example, rotating knives or another suitable arrangement, expediently into pieces whose length approximately equals the diameter of the extrudate. These cut-off melt particles cool in the stream of air or gas to such an extent that the surface is non-tacky on contact with other particles or a vessel wall but, on the other hand, the particles are still sufficiently plastic to assume a spherical shape owing to impacts, e.g. with the wall of a connected cyclone. This produces in a straightforward manner substantially spherical or lenticular particles with diameters of 0.5–4, preferably 0.8–2, mm. The preferred smaller particles are primarily suitable for filling capsules.

The invention makes it possible to produce, in a simple and environmentally friendly manner (without solvent), slow-release matrix pellets which release the active substance in a manner which can be controlled within wide limits. The release of active substance is delayed without application of a controlling film coating, which would have to be applied from organic solvents or aqueous dispersions and would require a drying step. The release of active substance takes place under erosion and diffusion control. The invention makes it possible to achieve pH-independent release of active substance too. The forms according to the invention are suitable for active substances with very different dissolving properties. The release-slowing effect can be adjusted extremely strictly even with small slow-release forms. The process makes it possible to produce solid solutions of the active substances in the matrix polymer by melt technology without using organic solvents. Solid solutions are distinguished by improved bioavailability. The process is very economic because it is continuous, and it is thus superior to traditional pelleting processes. The pellets according to the invention can have a high content of active substance. The variation in release of active substance is small and excellently reproducible because of the high homogeneity of the compositions. The kinetics of the release of active substance remain surprisingly stable (max 20% absolute difference in release, cf. Table II) even on storage under extreme climatic conditions (storage for at least 1 month at 50° C. or at 30° C. and 75% relative humidity).

The advantages of the extrusion process compared with other techniques such as granulation and tableting are that the technology is simple, solvents are avoided, the number and amount of auxiliaries are minimized, it is possible to produce solid solutions, and there is no possibility of the mixing of the components, in other words the individual slow-release forms have a reliably uniform composition throughout manufacture. There are also the advantages of a continuous process with high throughput and low material losses.

EXAMPLES

The parts by weight indicated in the table of active substance, polymers and lipophilic component and other auxiliaries were either premixed or introduced via separate weigh feeders directly into the feed section of a twin-screw extruder (Werner & Pfleiderer, ZSK 30). Melt extrusion took place with a product throughput of about 3–4 kg/h. The temperatures of the individual zones (sections) of the extruder were 30/150/100/100/100° C., the temperature of the heated die strip being indicated separately in the table. The die strip had 7 boreholes each 1 mm in diameter. The extrudates emerging through the heated die strip were pelleted by air-cooled hot-cut shaping using a granulator.

The release of active substance was measured by the USP XXI paddle method. This in vitro test method is used to determine the rate of dissolution of shaped articles containing active substances, e.g. tablets.

This was done by maintaining 900 ml of a phosphate buffer of pH 6.8 at 37° C. in a 1 l vessel with round bottom. A suitable amount of pellets (about 300 mg) 1.25–1.60 mm in size was weighed in. The percentage release of active substance from the pellets was determined in this USP XXI no-change test by UV spectroscopy after 1, 2, 3, 4, 5, 6, 7 and 8 hours with the paddle rotating at 100 rpm.

TABLE I

The active substance used in each of Examples 1 to 39 was 50% by weight gallopamil hydrochloride and in each of Examples 40 to 65 was 50% by weight theophylline.

| Example No. | Insoluble polymer b) | % | Lipophilic component c) | % | Gel former d) | % | Die temp. [° C.] | Release profile (% after 1 to 8 h) |
|---|---|---|---|---|---|---|---|---|
| 1 | Ethocel ® N 7 | 15 | Precirol ® Ato 5 | 10 | Klucel ® HF | 25 | 120 | 53/71/81/87/90/93/95/96 |
| 2 | " | 20 | " | 10 | " | 20 | 122 | 59/76/85/90/93/94/95/97 |
| 3 | " | 25 | " | 10 | " | 15 | 122 | 59/76/85/90/93/94/96/96 |
| 4 | " | 30 | " | 10 | " | 10 | 125 | 62/79/87/92/94/96/97/97 |
| 5 | " | 35 | " | 10 | " | 5 | 124 | 63/77/84/88/90/92/94/95 |
| 6 | " | 10 | " | 15 | " | 25 | 125 | 52/70/80/85/89/93/95/96 |
| 7 | " | 15 | " | 15 | " | 20 | 116 | 63/80/88/93/96/98/99/100 |
| 8 | " | 20 | " | 15 | " | 15 | 110 | 54/73/81/86/90/92/94/96 |
| 9 | " | 25 | " | 15 | " | 10 | 115 | 48/66/74/78/82/84/86/87 |
| 10 | " | 30 | " | 15 | " | 5 | 104 | 31/43/49/54/57/59/61/63 |
| 11 | " | 10 | " | 20 | " | 20 | 65 | 38/55/66/73/78/82/85/87 |

TABLE I-continued

The active substance used in each of Examples 1 to 39 was 50% by weight gallopamil hydrochloride and in each of Examples 40 to 65 was 50% by weight theophylline.

| Example No. | Insoluble polymer b) | % | Lipophilic component c) | % | Gel former d) | % | Die temp. [° C.] | Release profile (% after 1 to 8 h) |
|---|---|---|---|---|---|---|---|---|
| 12 | " | 15 | " | 20 | " | 15 | 67 | 32/46/56/62/67/71/74/76 |
| 13 | " | 20 | " | 20 | " | 10 | 88 | 28/39/46/51/54/57/59/61 |
| 14 | " | 25 | " | 20 | " | 5 | 87 | 21/28/32/36/38/39/41/42 |
| 15 | " | 10 | " | 25 | " | 15 | 65 | 29/43/51/57/61/64/67/79 |
| 16 | " | 15 | " | 25 | " | 10 | 61 | 23/33/40/45/48/50/52/55 |
| 17 | " | 20 | " | 25 | " | 5 | 59 | 17/23/27/30/33/34/35/38 |
| 18 | " | 10 | " | 30 | " | 10 | 58 | 23/34/41/46/50/53/55/57 |
| 19 | " | 15 | " | 30 | " | 5 | 59 | 22/32/39/43/56/48/49/51 |
| 20 | " | 10 | " | 35 | " | 5 | 53 | 16/22/26/29/31/32/34/36 |
| 21 | " | 10 | commercial long-chain partial glycerides | 20 | Klucel EF | 20 | 90 | 36/49/56/61/65/68/71/73 |
| 22 | " | 15 | commercial long-chain partial glycerides | 20 | " | 15 | 88 | 34/45/51/55/58/60/63/65 |
| 23 | " | 20 | commercial long-chain partial glycerides | 20 | " | 10 | 88 | 31/39/44/47/49/51/53/55 |
| 24 | " | 25 | commercial long-chain partial glycerides | 20 | " | 5 | 64 | 22/26/28/30/31/32/33/33 |
| 25 | Avicel PH 101 | 20 | commercial long-chain partial glycerides | 20 | Klucel HF | 10 | 118 | 69/88/96/100 |
| 26 | Ethylcellulose Type NF 100 | 10 | commercial long-chain partial glycerides | 20 | " | 20 | 109 | 39/56/65/71/76/79/82/84 |
| 27 | Ethylcellulose Type NF 100 | 15 | commercial long-chain partial glycerides | 20 | " | 15 | 110 | 24/37/46/52/60/62/64 |
| 28 | Ethylcellulose Type NF 100 | 20 | commercial long-chain partial glycerides | 20 | " | 10 | 110 | 20/27/32/34/37/38/40/41 |
| 29 | Ethylcellulose Type NF 100 | 25 | commercial long-chain partial glycerides | 20 | " | 5 | 110 | 15/20/22/23/24/25/26/28 |
| 30 | Ethylcellulose Type NF 7 | 20 | Polyglyceryl 3-distearate | 20 | " | 10 | 100 | 48/68/77/83/87/90/92/93 |
| 31 | Ethylcellulose Type NF 7 | 10 | Glycerol behenate | 20 | " | 20 | 100 | 33/54/67/76/83/87/92/94 |
| 32 | Ethylcellulose Type NF 7 | 15 | Glycerol behenate | 20 | " | 15 | 100 | 32/50/63/72/78/82/86/89 |
| 33 | Ethylcellulose Type NF 7 | 20 | Glycerol behenate | 20 | " | 10 | 103 | 34/49/58/65/69/73/76/78 |
| 34 | Ethylcellulose Type NF 7 | 25 | Glycerol behenate | 20 | " | 5 | 103 | 29/40/47/52/56/59/62/63 |
| 35 | Ethylcellulose Type NF 7 | 20 | Polyglycerol palmitostearate | 20 | " | 10 | 100 | 65/80/89/94/96/97/100/100 |
| 36 | Ethylcellulose Type NF 7 | 25 | Polyglycolized natural wax | 20 | " | 5 | 98 | 53/68/77/83/86/89/91/93 |
| 37 | Ethylcellulose Type NF 7 | 10 | Hydrogenated castor oil | 20 | " | 15 | 80 | 33/54/66/75/80/83/86/88 |
| 38 | Ethylcellulose Type NF 7 | 26 | Hydrogenated castor oil | 20 | " | 10 | 85 | 30/47/59/67/73/76/79/82 |
| 39 | Ethylcellulose Type NF 7 | 25 | Hydrogenated castor oil | 20 | " | 5 | 90 | 30/44/56/63/68/71/74/75 |
| 40 | Ethocel N7 | 10 | Precirol Ato5 | 20 | Klucel HF | 20 | 85 | 0/28/41/49/55/60/65/68/70 |
| 41 | " | 15 | " | 20 | " | 15 | 80 | 0/27/41/49/56/61/65/69/72 |
| 42 | " | 20 | " | 20 | " | 10 | 80 | 0/27/42/52/59/65/70/74/77 |
| 43 | " | 25 | " | 20 | " | 5 | 80 | 0/24/36/44/49/54/58/62/65 |
| 44 | " | 10 | " | 20 | Klucel EF | 20 | 80 | 0/53/74/85/92/95/98/100/100 |
| 45 | " | 15 | " | 20 | " | 15 | 85 | 0/45/61/72/79/85/89/92/93 |
| 46 | " | 20 | " | 20 | " | 10 | 85 | 0/26/35/42/47/51/54/58/61 |
| 47 | " | 25 | " | 20 | " | 5 | 80 | 0/17/23/27/30/32/34/36/38 |
| 48 | " | 15 | " | 25 | Klucel HF | 10 | 60 | 0/14/19/23/26/28/31/33/35 |
| 49 | " | 20 | " | 25 | " | 5 | 60 | 0/15/20/22/25/26/29/32/34 |
| 50 | Ethocel N7 | 15 | Precirol Ato5 | 30 | " | 5 | 60 | 0/9/13/15/17/19/21/23/25 |
| 51 | Ethocel NF100 | 10 | " | 20 | Klucel EF | 20 | 80 | 0/27/42/51/58/65/68/74/77 |
| 52 | " | 15 | " | 20 | " | 15 | 89 | 0/18/27/32/36/41/43/47/50 |
| 53 | " | 20 | " | 20 | " | 10 | 100 | 0/12/17/20/22/24/25/27/28 |
| 54 | " | 25 | " | 20 | " | 5 | 115 | 0/6/8/9/10/11/11/12/12 |
| 55 | " | 10 | " | 25 | " | 15 | 88 | 0/17/27/33/38/41/45/50/51 |

TABLE I-continued

The active substance used in each of Examples 1 to 39 was 50% by weight gallopamil hydrochloride and in each of Examples 40 to 65 was 50% by weight theophylline.

| Example No. | Insoluble polymer b) | % | Lipophilic component c) | % | Gel former d) | % | Die temp. [° C.] | Release profile (% after 1 to 8 h) |
|---|---|---|---|---|---|---|---|---|
| 56 | " | 15 | " | 25 | " | 10 | 95 | 0/11/16/20/23/25/27/30/31 |
| 57 | " | 20 | " | 25 | " | 5 | 100 | 0/7/10/11/13/14/15/16/16 |
| 58 | Ethocel N7 | 10 | hydrogenated castor oil | 20 | " | 20 | 105 | 0/52/76/88/93/95/97/98/99 |
| 59 | " | 15 | hydrogenated castor oil | 20 | " | 15 | 90 | 0/40/56/65/73/79/83/88/89 |
| 60 | " | 20 | hydrogenated castor oil | 20 | " | 10 | 87 | 0/27/39/48/54/59/64/69/72 |
| 61 | " | 25 | hydrogenated castor oil | 20 | " | 5 | 85 | 0/14/20/24/28/32/35/38/41 |
| 62 | Ethocel NF100 | 10 | hydrogenated castor oil | 20 | " | 20 | 99 | 0/39/59/74/82/90/93/97/100 |
| 63 | " | 15 | hydrogenated castor oil | 20 | " | 15 | 100 | 0/23/37/47/54/61/67/72/75 |
| 64 | " | 20 | hydrogenated castor oil | 20 | " | 10 | 110 | 0/13/16/24/29/32/35/38/40 |
| 65 | " | 25 | hydrogenated castor oil | 20 | " | 5 | 117 | 0/8/10/13/15/16/17/18/19 |

Ethocel ® = Ethylcellulose from Dow, USA
Precirol ® Ato5 = Long-chain partial glyceride from Gattefossé, France
Klucel ® = Hydroxypropylcellulose from Hercules, USA
Avicel = Microcrystalline cellulose from FMC, USA

TABLE II

Examples of the storage stability of the forms according to the invention

| Example No. | Release (% in 1 to 8 h) of the forms after storage (50° C. for 1 month) | Release (% after 1 to 8 h) of the forms after storage (30° C., 75% rel. humidity for 1 month) |
|---|---|---|
| 21 | 26/46/58/65/71/74/77/80 | 25/37/45/51/56/60/63/65 |
| 22 | 28/42/52/58/63/67/71/73 | 29/38/44/48/51/54/56/58 |
| 23 | 21/32/39/44/48/51/53/55 | 26/34/41/43/45/47/48 |
| 24 | 15/20/23/25/27/29/31/32 | 22/27/29/30/31/32/33/34 |
| 33 | 29/50/63/72/77/81/84/86 | 34/48/58/64/70/72/75/77 |
| 34 | 28/45/55/61/67/70/74/76 | 27/37/43/47/50/53/56/57 |
| 37 | 27/44/56/64/70/76/78/80 | 26/40/50/58/63/67/71/74 |
| 38 | 27/45/58/67/74/77/81/83 | 28/43/55/64/69/73/76/78 |
| 39 | 28/48/61/70/75/78/81/83 | 27/40/50/57/61/64/67/69 |

TABLE III

Comparative tests on the incomplete release from inert hydrophobic matrix without gel former

| Example No. | Active substance | | Insoluble polymer | % | Lipophilic component | % | Die temp. [° C.] | Release profile (% after 1 to 8 h) |
|---|---|---|---|---|---|---|---|---|
| 2 | Gallopamil hydrochloride | 50 | Ethylcellulose Type NF7 | | Precirol Ato5 | 15 | 107 | 18/22/25/27/29/30/31/32 |
| 3 | Gallopamil hydrochloride | 50 | Ethylcellulose Type NF7 | 35 | " | 20 | 87 | 15/19/21/22/23/24/25/25 |
| 4 | Gallopamil hydrochloride | 50 | Ethylcellulose Type NF7 | 30 | " | 25 | 74 | 17/21/25/27/29/30/31/32 |
| 5 | Gallopamil hydrochloride | 50 | Ethylcellulose Type NF7 | 25 | " | 30 | 56 | 19/26/32/35/37/38/40/40 |
| 6 | Gallopamil hydrochloride | 50 | Ethylcellulose Type NF7 | 20 | " | 35 | 57 | 15/21/26/29/30/31/33/33 |

TABLE III-continued

Comparative tests on the incomplete release from inert hydrophobic matrix without gel former

| Example No. | Active substance | Insoluble polymer | % | Lipophilic component | % | Die temp. [°C.] | Release profile (% after 1 to 8 h) |
|---|---|---|---|---|---|---|---|
| 7 | Gallopamil hydrochloride | Ethylcellulose Type NF7 | 50 15 | hydrogenated castor oil | 20 | 95 | 19/28/35/41/45/48/51/53 |
| 8 | Gallopamil hydrochloride | Ethylcellulose Type NF100 | 50 30 | Precirol Ato5 | 20 | 112 | 16/20/22/24/25/26/27 |
| 9 | Gallopamil hydrochloride | Ethylcellulose Type NF7 | 50 30 | Glycerol behenate | 20 | 103 | 25/33/37/40/42/44/46/47 |
| 10 | Theophylline | Ethylcellulose Type NF7 | 50 30 | Precirol Ato5 | 20 | 80 | 11/14/16/17/18/19/20/21 |
| 11 | " | Ethylcellulose Type NF100 | 50 30 | " | 20 | 125 | 3/4/4/5/5/5/5/6 |
| 12 | " | Ethylcellulose Type NF100 | 25 25 | " | 25 | 100 | 6/7/9/9/10/10/11/11 |
| 13 | " | Ethylcellulose Type NF100 | 50 30 | hydrogenated castor oil | 20 | 140 | 2/3/3/3/4/4/4/4 |
| 14 | " | Ethylcellulose Type NF7 | 50 30 | hydrogenated castor oil | 20 | 95 | 4/5/5/6/7/7/7/8 |

TABLE IV

Comparative tests on the storage stability (as disclosed in EP-B 0 024 596)

| Ex No. | Active substance | % | Insoluble polymer | % | Lipophilic component | % | Non-hydrophilic polymer II | % | Release profile (% after 1 to 8 h) A Immediately after production B Storage at 50° C. for 1 month |
|---|---|---|---|---|---|---|---|---|---|
| 1 | Gallopamil hydrochloride | 50 | Ethylcellulose Type NF7 | 10 | Precirol Ato5 | 20 | Vinylpyrrolidone/ vinyl acetate copolymer (Kollidon ® VA64) | 20 | A 45/60/67/72/76/78/81/83 B 52/69/76/81/84/86/88/90 |
| 2 | Gallopamil hydrochloride | 50 | Ethylcellulose Type NF7 | 15 | " | 20 | Vinylpyrrolidone/ vinyl acetate copolymer (Kollidon ® VA64) | 15 | A 35/47/52/56/60/63/66/68 B 41/62/72/76/79/81/83/84 |
| 3 | Gallopamil hydrochloride | 50 | Ethylcellulose Type NF7 | 20 | " | 20 | Vinylpyrrolidone/ vinyl acetate copolymer (Kollidon ® VA64) | 10 | A 27/35/39/42/44/45/47/48 B 28/44/54/61/67/70/73/75 |
| 4 | Gallopamil hydrochloride | 50 | Ethylcellulose Type NF7 | 25 | " | 20 | Vinylpyrrolidone/ vinyl acetate copolymer (Kollidon ® VA64) | 5 | A 22/28/31/33/34/35/36/36 B 14/24/32/38/43/47/51/54 |

We claim:

1. Slow-release matrix pellets with a spherical or lenticular shape and uniform maximum diameters in the range of from 0.5 to 4 mm, said pellets comprising a) 0.1–87% by weight of at least one biologically active compound, b) 5–50% by weight of ethylcellulose, c) 5–45% by weight of at least one water insoluble lipophilic compound as plasticizer for polymer b) and lubricant, selected from the group consisting of mono-, di- triglycerides or mixtures thereof and polyglycerol fatty acid esters, D) 3–40% by weight of a water soluble cellulose derivative as a gel-forming polymer which breaks up the release-slowing matrix by swelling of the ethylcellulose, said pellets being obtained by extrusion of a solvent-free molten mixture of the components at a temperature of from 50 to 200° C. and continuous shaping.

2. Slow-release matrix pellets as claimed in claim 1, having the following concentrations of the components:

a) 1–75% by weight, b) 10–40% by weight, c) 10–35% by weight, d) 5–25% by weight.

3. Slow-release matrix pellets as claimed in claim 1, wherein the maximum diameter is 0.8–2 mm.

4. Slow-release matrix pellets as claimed in claim 1 or 2, wherein the active substance (a) is pharmaceutical in nature.

5. A continuous one-stage process for producing slow-release matrix pellets as claimed in claim 1 or 2 by extrusion of the molten mixture of the components at 50–200° C. and continuous shaping.

6. A process as claimed in claim 5, wherein extrusion is carried out at 50–180° C.

7. A process as claimed in claim 5, wherein extrusion is carried out at 60–150° C.

8. A process as claimed in claim 5, wherein hot-cut shaping takes place.

9. Slow release pellets as claimed in claim 1, which after storage for one month at 50° C., release from 15 to 29% of said biologically active compound in one hour and from 29 to 81%, respectively, after six hours.

* * * * *

UNITED STATES PATENT AND TRADEMARK OFFICE
CERTIFICATE OF CORRECTION

PATENT NO. : 6,290,990 B1
DATED : September 18, 2001
INVENTOR(S) : Grabowski et al.

It is certified that error appears in the above-identified patent and that said Letters Patent is hereby corrected as shown below:

Title page,
Item [22], "Apr. 15, 1995" should be -- Apr. 5, 1995 --.

Signed and Sealed this

Twenty-sixth Day of February, 2002

*Attest:*

JAMES E. ROGAN
*Attesting Officer*     *Director of the United States Patent and Trademark Office*